(12) United States Patent
Teranishi et al.

(10) Patent No.: US 6,302,872 B1
(45) Date of Patent: Oct. 16, 2001

(54) ABSORBENT MEMBER SEALED BETWEEN A TOPSHEET AND A BACKSHEET

(75) Inventors: Futoshi Teranishi; Hiroyuki Yokomatsu; Satoshi Tanaka; Miyuki Kondo; Mitsugu Hamajima; Minoru Nakanishi, all of Tochigi-ken (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/609,391

(22) Filed: Jul. 3, 2000

(30) Foreign Application Priority Data

Jul. 8, 1999 (JP) .................................. 11-194672

(51) Int. Cl.⁷ ................................................. A61F 13/15
(52) U.S. Cl. .................... 604/385.23; 604/367; 604/372; 604/385.16; 604/385.22
(58) Field of Search ................................. 604/367, 372, 604/385.16, 385.22, 385.23

(56) References Cited

FOREIGN PATENT DOCUMENTS

| 61179307 | 8/1986 | (JP) . |
| 8164164 | 6/1996 | (JP) . |
| 9206331 | 8/1997 | (JP) . |
| 1075978 | 3/1998 | (JP) . |

*Primary Examiner*—Aaron J. Lewis
*Assistant Examiner*—Michael Bogart

(57) ABSTRACT

An absorbent article having a liquid permeable topsheet 2, a liquid impermeable backsheet 3, and a liquid retentive absorbent member 4 interposed between the topsheet 2 and the backsheet 3, the topsheet 2 and the backsheet 3 being joined by sealing to form sealed parts S, in which the backsheet has a tear strength of 120 to 500 cN.

5 Claims, 2 Drawing Sheets

Figure 3:
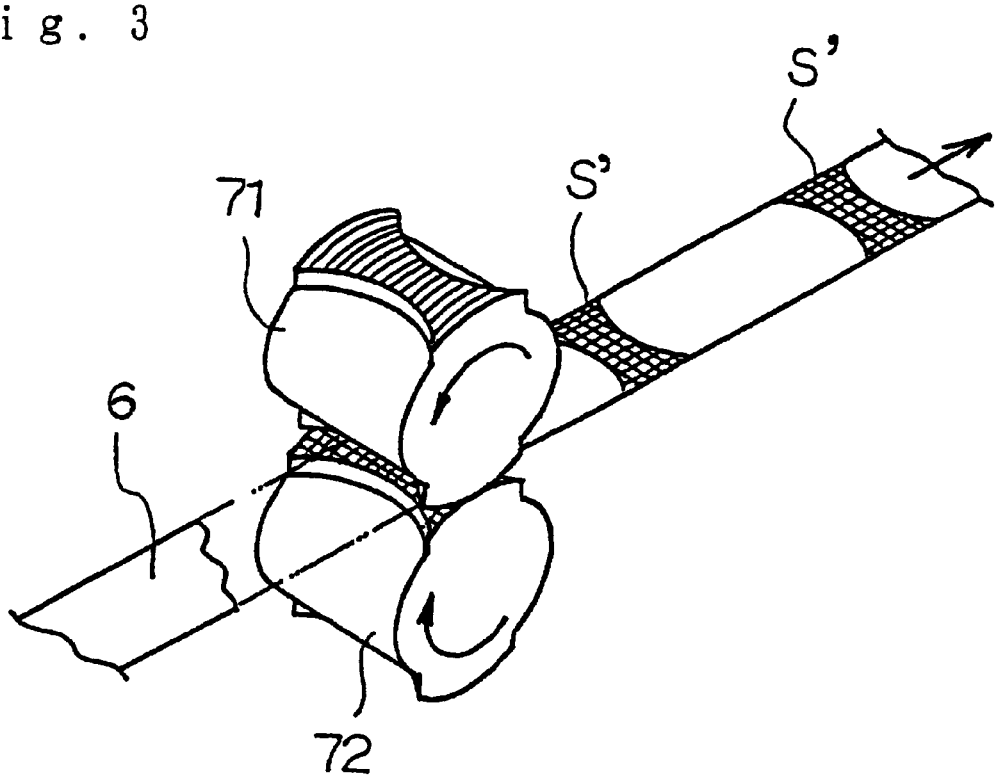

Fig. 1
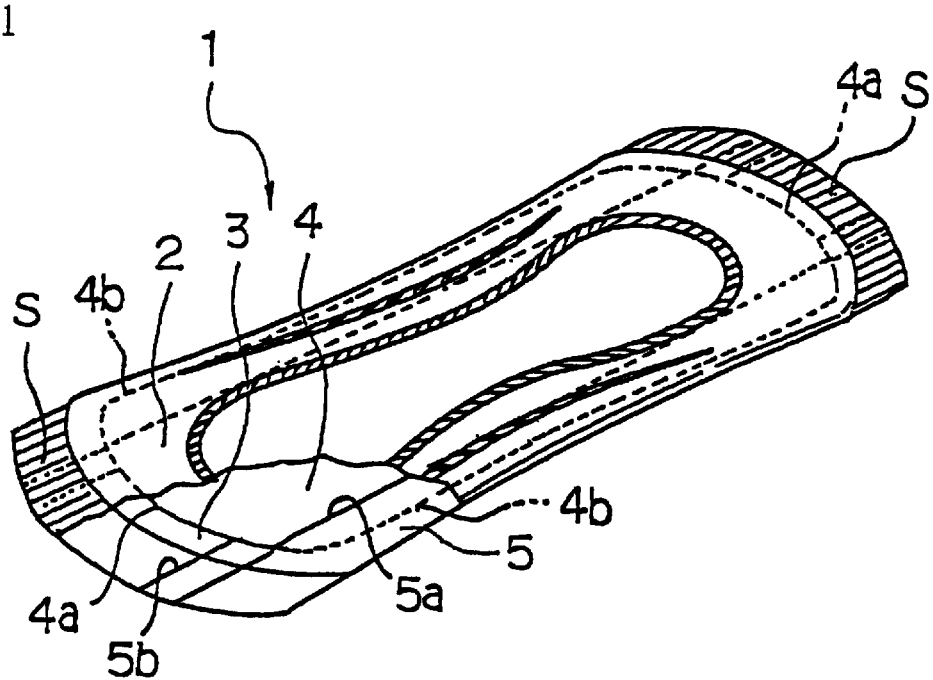
Fig. 2(a)
Fig. 2(b)
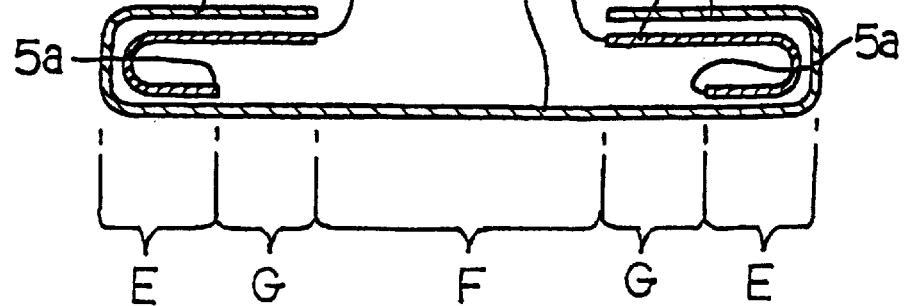

ABSORBENT MEMBER SEALED BETWEEN A TOPSHEET AND A BACKSHEET

BACKGROUND OF THE INVENTION

The present invention relates to absorbent articles, such as sanitary napkins, disposable diapers, urinary incontinent pads, panty liners, underlaying sheets for pets, and the like. More particularly, it relates to absorbent articles which are free from adhesion failure or damage in their sealed parts and are therefore excellent in appearance and leakproofness.

Absorbent articles, such as sanitary napkins, having a liquid permeable topsheet, a liquid impermeable backsheet, and a liquid retentive absorbent member interposed between the topsheet and the backsheet are widely known. The topsheet and the backsheet are joined together in their peripheries with an adhesive or by heat sealing, ultrasonic sealing and the like thereby to form a sealed part. Although it is desirable to use no, or a small amount of, an adhesive from the standpoint of speeding up of the production line and economy, the joining method by heat sealing or ultrasonic sealing tends to bring about sealing defects such as an adhesion failure (lifting or separation) or damage such as a cut, which may lead to deteriorated appearance or leakage. Such sealing defects or damage are particularly liable to occur in cases where the sealed part has a difference in level or basis weight due to, for example, other sheeting members disposed between the topsheet and the backsheet.

In connection with the backsheet of the absorbent article, Japanese Patent Laid-Open Publication No. 61-179307 discloses a backsheet made of a polyolefin resin composition having an Elmendorf tear strength of 15 kg.cm/cm$^2$ or more. Japanese Patent Laid-Open Publication No. 9-206331 discloses a backing material made of a porous sheet having a tensile yield strength of 120 kg/cm$^2$ or more. However, since no consideration is given to the heat sealing properties in these Publications at all, there is a fear that adhesion failures and damage in the sealed part occur in the absorbent articles using the backsheets disclosed therein.

Japanese Patent Laid-Open Publication No. 10-75978 discloses to provide a non-skin contact layer formed by extensible and/or stretchable materials containing films obtained by catalysis of metallocene for the purpose of an easy fit to the body or prevention of the occurrence of misposiioning in use. Japanese Patent Laid-Open Publication No. 8-164164 discloses to use in a shorts type throwaway diaper a backsheet having a strength of 1500 gf/50 mm or more in the transverse direction of the diaper, aiming to enhance the ease of tearing joint parts of the both sides. However, the extensible materials and backsheets disclosed in this publication are a composite material of nonwoven fabric, which makes it difficult to produce absorbent articles inexpensively.

SUMMARY OF THE INVENTION

An object of the present invention is to provide an absorbent article which substantially eliminates adhesion failures, such as lifting or separation, and damage, such as cuts and tears, and secures excellent appearance and leakproofness.

The above object is accomplished by an absorbent article having a liquid permeable topsheet, a liquid impermeable backsheet, and a liquid retentive absorbent member interposed between the topsheet and the backsheet, the topsheet and the backsheet being joined by sealing to form a sealed part, in which the backsheet has a tear strength of 120 to 500 cN.

BRIEF DESCRIPTION OF THE ACCOMPANYING DRAWINGS

The present invention will become more fully understood from the detailed description given hereinbelow and the accompanying drawings which are given by way of illustration only, and thus are not limitative of the present invention, and wherein:

FIG. 1 is a perspective view of a sanitary napkin as an embodiment of the absorbent article according to the present invention, a part of which is cut away.

FIGS. 2(a) and 2(b) show one of the sealed parts of the sanitary napkin of FIG. 1, wherein FIG. 2(a) is a back side view of the sealed part, and FIG. 2(b) is a cross-sectional view taken along lines A–B, B–C and C–D of FIG. 2(a).

DETAILED DESCRIPTION OF THE PREFERRED EMBODIMENTS

The present invention will be described in detail with reference to a preferred embodiment in the practice of the present invention. The sanitary napkin 1 shown in FIG. 1 is substantially rectangular and has a liquid permeable topsheet 2, a liquid impermeable backsheet 3, and a liquid retentive absorbent member 4 interposed between these sheets.

The absorbent member 4 is substantially rectangular in its plan view and is superposed on the backsheet 3. The topsheet 2, which is to be brought into contact with a wearer's skin, has a larger contour than the absorbent member 4. Both sides of the topsheet 2 are folded inward to cover the sides of the absorbent member 4, and both edges of the topsheet 2 extend outward over the ends 4a and 4a of the absorbent member 4. The backsheet 3 is almost equal in width to the folded topsheet 2. Both edges of the backsheet 3 extend outward over the edges 4a and 4a of the absorbent member 4.

The extensions of the topsheet 2 and the backsheet 3 over the edges 4a and 4a of the absorbent member 4 are heat-sealed to each other to form an almost symmetrical pair of sealed parts S and S on both edges of the sanitary napkin 1.

As shown in FIG. 2, each sealed part S comprises regions E, F and G which are different in basis weight. Since there is a leakproof sheet 5, which is an independent member, and the folded part 21 of the topsheet 2 interposed in parts between the topsheet 2 and the backsheet 3, the sealed part S comprises a 5-ply region E having the greatest basis weight, a 2-ply region F having the smallest basis weight, and a 4-ply region G whose basis weight is midway between the regions E and F. The difference in basis weight between the regions E and F is 15 g/m$^2$ or more.

The leakproof sheet 5 is a liquid impermeable sheet of band form. As illustrated in FIG. 1, the leakproof sheet 5 is disposed on each side portion of the sanitary napkin 1 over the whole length of the napkin 1 in such a manner that each side portion 4b of the absorbent member 4 is covered therewith, one side 5a of which is on the wearer's skin side, and the other side 5b of which is on the back side of the absorbent member 4.

The layer structure of each sealed part S is the same as that of the main body of the sanitary napkin 1, except that there is not the absorbent member 4. That is, as shown in FIG. 2B, there are the folded part 21 of the topsheet 2 and the leakproof sheet 5 in parts between the topsheet 2 and the backsheet 3. The two leakproof sheets 5 are separate at a certain distance on each of the skin side and the back side, with the distance between the sides 5b and 5b on the back side being shorter than that between the sides 5a and 5a on the skin side.

The backsheet 3 has a tear strength of 120 to 500 cN. If the tear strength of the backsheet 3 is less than 120 cN, the sealed part S is liable to a damage such as a cut or a hole. If it exceeds 500 cN, the sealed part S, especially the region F or G of small basis weight, is apt to suffer from adhesion failure. To secure prevention of such a damage and an adhesion failure, it is preferred for the backsheet 3 to have a tear strength of 150 to 400 cN. The terminology "tear strength" as used herein denotes an Elmendorf tear strength measured in accordance with JIS K7128. The language "the backsheet has a tear strength of 120 to 500 cN" is intended to mean that at least the parts to be sealed of the backsheet has that tear strength.

To prevent a damage and an adhesion failure of the sealed parts S, it is preferred for the backsheet 3 to have an elongation of 3 to 35%, particularly 3 to 20%, under a load of 200 gf/10 mm. The elongation under a load of 200 gf/10 mm is obtained by a tensile test in which a sample having a length of 100±10 mm in agreement with the machine direction (MD) and a width of 10±1 mm in agreement with the crosswise direction (CD) is pulled between chucks at a distance of 50 mm at a speed of 300 mm/min up to a maximum load of 2000 gf in the machine direction, and the elongation (%) with a load of 200 gf applied is measured in the course of pulling.

The backsheet 3 preferably comprises a resin composition containing a resin having a weight average molecular weight (Mw) to number average molecular weight (Mn) ratio of 1.5 to 4 (hereinafter the specific Mw/Mn ratio will be referred to as molecular weight distribution (A)).

Resins having the molecular weight distribution A include polyethylene, polypropylene, polyvinyl acetate, and mixtures thereof. Polyolefin resins obtained by using a metallocene catalyst are preferred. In particular, polyethylene, an ethylene-α-olefin copolymer, and a propylene-α-olefin copolymer are preferred. The α-olefins include those having 3 to 30 carbon atoms, e.g., propylene, 1-butene, 1-pentene, 1-hexene, 1-octene, 1-heptene, 4-methyl-1-pentene, 4-methyl-1-hexene, 4,4-dimethyl-1-pentene, and octadecene, with 1-hexene, 1-octene, 1-heptene, and 4-methyl-1-pentene being particularly preferred. The ethylene-α-olefin copolymer preferably has an ethylene content of 40 to 98% by weight and an α-olefn content of 2 to 60% by weight. The metallocene catalyst as referred to above denotes a compound comprising a pair of unsaturated cyclic moieties having a transition metal sandwiched therebetween, typically exemplified by cyclopentadienyl complexes.

The resin having the molecular weight distribution (A) is preferably used in combination with other resin(s) different in molecular weight distribution so as to improve machinability in cutting operation and to improve the sheet strength. The proportion of the resin having the molecular weight distribution (A) in the total resin is preferably 5 to 90% by weight, still preferably 10 to 70%. The other resins different in molecular weight distribution include low-density polyethylene, medium-density polyethylene, high-density polyethylene, polypropylene, polyurethane, polyester, and polyethylene. The resin composition can contain white pigments, such as titanium oxide, talc and calcium carbonate, or other colorants for the purpose of coloring the backsheet 3.

The backsheet 3 preferably has a basis weight of 15 to 50 g/m². From the balance between the cost and the film strength, a basis weight of 18 to 30 g/m² is still preferred. The backsheet 3 is preferably a single film from the economical consideration but may be laminated with nonwoven fabric, etc. for the purpose of improving the texture, and the like.

The backsheet 3 in this embodiment is formed only of a single layer film material obtained by the aforesaid resin compositions, and both the skin side and the back side of the film material each are not covered with nonwoven fabric.

This constitution makes it possible to restrain the amount of an adhesive to be applied for fixing to the clothes and to produce inexpensively.

To secure prevention of a damage or an adhesion failure of the sealed parts S, it is preferred for the backsheet 3 to have a density of 0.900 to 0.960 g/cm³, particularly 0.91 to 0.94 g/cm³, and a melt index (MI) of 2 to 20 g/10 min, particularly 3 to 15 g/10 min. The MI is measured in accordance with ASTM D-1238.

The sanitary napkin 1 can be produced, for example, as follows. Continuous sheets for the topsheet 2, the backsheet 3, and the leakproof sheets 5 and 5 are superposed on each other with a plurality of absorbent members 4 being arranged inside with regular spacing to form a laminate structure 6 shown in FIG. 3, in which the portion having no absorbent member (i.e., the portion between adjacent absorbent members) has the layer structure shown in FIG. 2B. The laminate structure 6 is passed through a pair of hot rolls 71 and 72 of a heat sealer so that the portions having no absorbent member 4 are heat-sealed to form sealed parts S' as shown in FIG. 3. The continuous laminate structure thus heat-sealed is cut to size at each sealed part S' to give the cut edge contour shown in FIG. 2A. Usually, a pressure-sensitive adhesive (not shown) is applied to the back side of the backsheet 3 in a convenient stage of the production line, with which the napkin 1 may be attached to underwear, and a release sheet (not shown) is applied on the adhesive layer.

Having the backsheet 3 with a tear strength of 120 to 500 cN, the sanitary napkin 1 according to the above-described embodiment hardly suffers from damage such as cuts and holes or adhesion failures such as lifting at the sealed parts S which are formed by application of heat, ultrasonic waves, pressure or a combination thereof. For example, even where a plurality of sanitary napkins 1 are produced by continuous high-speed heat sealing as in the above-described production process, the sealed parts S are free from damage or adhesion failures.

The topsheet 2 and the absorbent member 4 can be of various materials and structures used in conventional absorbent articles. For example, the topsheet is preferably of nonwoven fabric comprising thermoplastic synthetic fiber. The leakproof sheets 5 can be of any known materials having leakproofness. For example, nonwoven fabric having a water repellent finish or a thermoplastic resin film are preferred.

The present invention is not limited to the aforementioned embodiment, and various modifications can be made therein. For example, the pair of the leakproof sheets can be omitted. Both the topsheet 2 and the backsheet 3 can extend outward from all the periphery of the absorbent member 4 to form a continuous sealed part around the absorbent member 4. In the sealed part, the topsheet and the backsheet do not need to be joined with direct contact with each other. As stated previously, the backsheet does not need to satisfy the essentially required tear strength all over the entire area thereof as long as at least the parts to be sealed has the specific tear strength. The same applies to the other preferred physical properties of the backsheet. The present invention is applicable to not only sanitary napkins but other absorbent articles such as disposable diapers, adult incontinent pads, panty liners, underlaying sheets for pets, and the like.

EXAMPLES

Example 1

Preparation of Resin Material

Polyethylene prepared by using a metallocene catalyst (Evolue SP2040, available from Mitsui Petrochemical Industries, Ltd.; density: 0.920 g/cm$^3$; hereinafter referred to as resin A) was stirred in a Henschel mixer and kneaded and pelletized in a twin-screw extruder (PCM-45-33.5, supplied by Ikegai Tekko Corp.; diameter: 45 mm) at a set temperature of 160° C. and at a screw revolution speed of 150 rpm to prepare pellets of resin A. The molecular weight distribution (Mw/Mn) of Evolue SP2040 is 2.10.

Film Formation

The pellets of resin A was blow molded by means of a blow molding machine having a single screw extruder (diameter: 50 mm; L/D: 28) and a circular die (diameter: 100 mm; die lip clearance: 1.0 mm) at a set temperature of 160° C., a throughput of 25 kg/hr, and a blow-up ratio of 2.5 to obtain blown tubing having a film thickness of 0.03 mm and a flat width of 380 mm, which was cut open to obtain a continuous film having a basis weight of 20 g/m$^2$ and a density of 0.920 g/cm$^3$.

Production of Sanitary Napkins

Sanitary napkins shown in FIGS. 1 and 2 were produced in a continuous manner by using the continuous film prepared above as a backsheet 3 in accordance with the above-described process. A continuous nonwoven fabric sheet made of core/sheath conjugate fiber comprising polyethylene terephthalate as a core and polyethylene as a sheath was used as a topsheet 2, and a continuous waterproof sheet (wet processed absorbent paper laminated with polyethylene) was used as leakproof sheets 5. The absorbent member 4 was prepared by enveloping a mixture of fluff pulp and super-absorbent polymer particles in absorbent paper.

Example 2

A resin composition was prepared in the same manner as in the preparation of the resin material of Example 1, except that 70 wt % of resin A and 30 wt % of linear low-density polyethylene (Ultzex 3520, available from Mitsui Petrochemical Industries, Ltd.; density: 0.940 g/cm$^3$; hereinafter referred to as resin B) were mixed in a Henschel mixer. A blown film having a thickness of 0.05 mm, a basis weight of 30 g/m$^2$, and a density of 0.925 g/m$^3$ was prepared from the resulting resin pellets in the same manner as in Example 1. Sanitary napkins were produced by using the film as a backsheet in the same manner as in Example 1.

Example 3

A blown film having a thickness of 0.04 mm, a basis weight of 25 g/m$^2$, and a density of 0.930 g/cm$^3$ was prepared in the same manner as in Example 2, except for using 30 wt % of resin A and 70 wt % of resin B. Sanitary napkins were produced by using the resulting film as a backsheet in the same manner as in Example 1.

Example 4

A blown film having a thickness of 0.04 mm, a basis weight of 25 g/m$^2$, and a density of 0.926 g/cm$^3$ was prepared in the same manner as in Example 2, except for using 70 wt % of resin A and 30 wt % of high-density polyethylene (Hizex 2208J, available from Mitsui Petrochemical Industries, Ltd.; density: 0.968 g/cm$^3$; hereinafter referred to as resin C). Sanitary napkins were produced by using the resulting film as a backsheet in the same manner as in Example 1.

Comparative Example 1

A blown film having a thickness of 0.04 mm, a basis weight of 25 g/m$^2$, and a density of 0.940 g/cm$^3$ was prepared in the same manner as in Example 1, except for using resin B in place of resin A. Sanitary napkins were produced by using the resulting film as a backsheet in the same manner as in Example 1.

Comparative Example 2

A blown film having a thickness of 0.03 mm, a basis weight of 20 g/m$^2$, and a density of 0.968 g/cm$^3$ was prepared in the same manner as in Example 1, except for using resin C in place of resin A. Sanitary napkins were produced by using the resulting film as a backsheet in the same manner as in Example 1.

Comparative Example 3

A blown film having a thickness of 0.05 mm, a basis weight of 30 g/m$^2$, and a density of 0.937 g/cm$^3$ was prepared in the same manner as in Example 2, except for using 70 wt % of resin B and 30 wt % of resin C. Sanitary napkins were produced by using the resulting film as a backsheet in the same manner as in Example 1.

Comparative Example 4

A blown film having a thickness of 0.04 mm, a basis weight of 25 g/m$^2$, and a density of 0.940 g/cm$^3$ was prepared in the same manner as in Example 2, except for using 50 wt % of resin B, 30 wt % of resin C, and 20 wt % of low-density polyethylene (Mirason 11P, available from Mitsui Petrochemical Industries, Ltd.; density: 0.917 g/cm$^3$). Sanitary napkins were produced by using the resulting film as a backsheet in the same manner as in Example 1.

Comparative Example 5

A blown film having a thickness of 0.04 mm, a basis weight of 25 g/m$^2$, and a density of 0.870 g/cm$^3$ was prepared in the same manner as in Example 1, except for replacing resin A with polyethylene prepared by using a metallocene catalyst (Affinity EG8200, available from Dow Chemical Co., Ltd.; density: 0.870 g/cm$^3$). Sanitary napkins were produced by using the resulting film as a backsheet in the same manner as in Example 1.

The Elmendorf tear strength of the films prepared in Examples and Comparative Examples was measured with Elmendorf Tearing Tester manufactured by Toyo Seiki Seisakusyo. The measurement was made at 20° C. and 65% RH in accordance with JIS K7128. The results obtained are shown in Tables 1 and 2 below. Measurement is made five times for each sample to obtain an average value.

Further, the MD elongation (%) under a load of 200 gf/10 mm was measured in accordance with the above-described method. The results obtained are also shown in Tables 1 and 2. Measurement was made at 20° C. and 65% RH using TENSILON tensile tester (manufactured by Toyo Baldwin Co., Ltd. Type: RTM-25) five times for each sample and an average value is shown in Tables.

Tables 1 and 2 also show the molecular weight distribution (Mw/Mn) and the melt index (MI) of the films measured as follows.

Measurement of Molecular Weight Distribution (Mw/Mn)

A sample resin or resin composition was dissolved in orthodichlorobenzene (ODCB) (available from Wako Pure Chemical Industries, Ltd.) while hot (140° C.) to prepare a 0.1 wt % resin solution. The solution was analyzed by gel-permeation chromatography (GPC) using the following instruments and conditions.

GP chromatograph: High-speed GP chromatograph HLC-8020, manufactured by Toso Corp.

Separation column: Polystyrene gel TSKgel $GMH_{HR}$-H HT, supplied by Toso Corp.; column size: 72 mm (D)×600 mm (H)

Mobile phase: ODCB containing 0.025 wt % antioxidant BHT (available from Takeda Chemical Industries, Ltd.)

Temperature of mobile phase and column: 140° C.

Flow rate: 1.0 ml/min

Sample solution: 500 μl

Detector: differential refractometer (RI) built in the GPC equipment

A calibration curve was prepared by using mono-dispersed standard polystyrene (TSK Standard Polystyrene available from Toso Corp.), from which the weight average molecular weight (Mw) and the number average molecular weight (Mn) of the sample were calculated.

Measurement of MI

Measured in accordance with ASTM D-1238. Conditions of 230° C. and 2.16 kgf were applied to polypropylene resins and block copolymers, and conditions of 190° C. and 2.16 kgf were applied to polyethylene resins.

The appearance of the sealed parts of the sanitary napkins was observed and rated according to the following standard. A hundred napkins per (Comparative) Example were evaluated. The results are shown in Tables 1 and 2. In Tables, "E region" means the region E having the greatest thickness and basis weight, and "F region" means the region F having the smallest thickness and basis weight.

[Evaluation of Appearance of Sealed Part]

100 samples of the sanitary napkins for each of Examples and Comparative Examples were observed with eyes to detect the lifting or cuts caused by sealing failure on the sealed parts S, S of each sample, and the results were shown in accordance with the following standard.

Standard of Evaluation

A . . . All the 100 samples are free from lifting or cuts.

B . . . One or more out of 100 samples suffer from either lifting or a cut.

C . . . One or more out of 100 samples suffer from both lifting and a cut.

By the term "lifting" is meant that there is an unsealed part of 0.01 $cm^2$ or larger. By the term "cut" is meant that the backsheet has a cut of 2 mm or longer.

TABLE 1

| Example No. | Composition Component | wt % | Molecular weight Distribution (Mw/Mn) | MI (g/10 min) | Density (g/cm³) | Tear Strength | MD Elongation (200 gf/10 mm load) (%) | Region E Thickness (mm) | Region E Basis Wt. (g/m²) | Region F Thickness (mm) | Region F Basis Wt. (g/m²) | Difference between E and F Thickness (mm) | Difference between E and F Basis Wt. (g/m²) | Appearance |
|---|---|---|---|---|---|---|---|---|---|---|---|---|---|---|
| 1 | Evolue SP2040 | 100 | 2.10 | 4.0 | 0.920 | 357 | 11.6 | 0.63 | 106 | 0.35 | 61 | 0.28 | 45 | A |
| 2 | Evolue SP2040 | 70 | 2.37 | 3.4 | 0.925 | 348 | 6.1 | 0.65 | 126 | 0.10 | 30 | 0.55 | 96 | A |
|   | Ultzex 3520 | 30 | | | | | | | | | | | | |
| 3 | Evolue Sp2040 | 30 | 2.73 | 2.6 | 0.930 | 210 | 6.5 | 0.64 | 111 | 0.24 | 45 | 0.4 | 66 | A |
|   | Ultzex 3520 | 70 | | | | | | | | | | | | |
| 4 | Evolue SP2040 | 70 | 3.18 | 4.4 | 0.926 | 281 | 5.7 | 0.75 | 136 | 0.65 | 116 | 0.1 | 20 | A |
|   | Hizex 2208J | 30 | | | | | | | | | | | | |

TABLE 2

| Comp. Example No. | Composition Component | wt % | Molecular weight Distribution (Mw/Mn) | MI (g/10 min) | Density (g/cm³) | Tear Strength | MD Elongation (200 gf/10 mm load) (%) | Region E Thickness (mm) | Region E Basis Wt. (g/m²) | Region F Thickness (mm) | Region F Basis Wt. (g/m²) | Difference between E and F Thickness (mm) | Difference between E and F Basis Wt. (g/m²) | Appearance |
|---|---|---|---|---|---|---|---|---|---|---|---|---|---|---|
| 1 | Ultzex 3520 | 100 | 3.00 | 2.1 | 0.940 | 112 | 4.5 | 0.64 | 111 | 0.24 | 98 | 0.4 | 13 | B* |
| 2 | Hizex 2208J | 100 | 5.71 | 5.2 | 0.968 | 41 | 3.1 | 0.67 | 116 | 0.35 | 70 | 0.32 | 46 | C |

TABLE 2-continued

| | Backsheet | | | | | | | Sealed Part | | | | | | |
|---|---|---|---|---|---|---|---|---|---|---|---|---|---|---|
| | | | Molecular | | | | | MD Elongation | Region E | | Region F | | Difference between E and F | |
| Comp. Example No. | Composition Component | wt % | weight Distribution (Mw/Mn) | MI (g/10 min) | Density (g/cm³) | Tear Strength | (200 gf/10 mm load) (%) | Thickness (mm) | Basis Wt. (g/m²) | Thickness (mm) | Basis Wt. (g/m²) | Thickness (mm) | Basis Wt. (g/m²) | Appearance |
| 3 | Ultzex 3520 | 70 | 3.81 | 3.0 | 0.937 | 88 | 4.3 | 0.66 | 118 | 0.25 | 50 | 0.41 | 68 | C |
| | Hizex 2208J | 30 | | | | | | | | | | | | |
| 4 | Ultzex 3520 | 50 | 5.24 | 4.3 | 0.940 | 89 | 3.9 | 0.65 | 121 | 0.31 | 35 | 0.34 | 86 | C |
| | Hizex 2208J | 30 | | | | | | | | | | | | |
| | Mirason 11P | 20 | | | | | | | | | | | | |
| 5 | Affinity EG8200 | 100 | 2.00 | 5.0 | 0.870 | 515 | 39.8 | 0.64 | 111 | 0.33 | 40 | 0.31 | 71 | B** |

Note:
*A cut was observed
**Lifting was observed

As is apparent from the results in Tables 1 and 2, the sanitary napkins of Examples hardly suffer from lifting or cutting in the sealed parts thereof as compared with the comparative napkins.

As described above, the absorbent article according to the present invention hardly suffers from adhesion failures or damage in the sealed parts thereof even where the topsheet and the backsheet are joined together by sealing with or without an adhesive and is therefore excellent in appearance and leakproofness.

What is claimed is:

1. An absorbent article having a liquid-permeable topsheet, a liquid-impermeable backsheet and a liquid-retentive absorbent member interposed between the top sheet and the backsheet, the topsheet and the backsheet being joined by sealing to form a sealed part, wherein said backsheet has a tear strength of 120 to 500 cN and an elongation of 3 to 20% under a load of 200 gf/10 mm.

2. An absorbent article according to claim 1, wherein said backsheet comprises a plurality of resins different in molecular weight distribution, and contains a resin having a molecular weight distribution of 1.5 to 4 in terms of a weight average molecular weight to number average molecular weight ratio in a proportion of 5 to 90% by weight based on the total resin.

3. An absorbent article according to claim 2, wherein said resin having a molecular weight distribution of 1.5 to 4 is a polyolefin resin prepared by using a metallocene catalyst.

4. An absorbent article according to claim 1, wherein said sealed part comprises a plurality of regions different in basis weight, and the difference in basis weight between the region having the greatest basis weight and the region having the smallest basis weight is 15 g/m² or more.

5. An absorbent article according to claim 1, wherein said backsheet consists of a single layer film material.

* * * * *